(12) United States Patent
Broussard et al.

(10) Patent No.: US 6,667,418 B2
(45) Date of Patent: Dec. 23, 2003

(54) OXIDATION TREATMENT OF A RECYCLE STREAM IN PRODUCTION OF ACETIC ACID BY METHANOL CARBONYLATION

(75) Inventors: Jerry A. Broussard, Marietta, GA (US); Hung-Cheun Cheung, Corpus Christi, TX (US); Stephen Andrew Houliston, Ottumwa, IA (US); Michael E. Huckman, Corpus Christi, TX (US); Peggy McKarns Macatangay, Corpus Christi, TX (US); Madan Singh, Corpus Christi, TX (US); Michael L. Karnilaw, Houston, TX (US); G. Paull Torrence, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 99 days.

(21) Appl. No.: 10/124,200

(22) Filed: Apr. 16, 2002

(65) Prior Publication Data

US 2003/0199711 A1 Oct. 23, 2003

(51) Int. Cl.[7] ............................................. C07C 51/12
(52) U.S. Cl. ..................... 562/519; 562/608; 562/607
(58) Field of Search ......................... 562/519, 608, 562/607

(56) References Cited

U.S. PATENT DOCUMENTS 3,769,329 A   10/1973   Paulik et al. ............... 260/488
5,001,259 A   3/1991    Smith et al. ................ 562/519
5,026,908 A   6/1991    Smith et al. ................ 562/519
5,144,068 A   9/1992    Smith et al. ................ 562/519
5,155,265 A * 10/1992   Scates et al. ............... 562/608
5,155,266 A * 10/1992   Scates et al. ............... 562/608
5,202,481 A * 4/1993    Scates et al. ............... 562/608
5,625,095 A   4/1997    Miura et al. ................ 562/519

OTHER PUBLICATIONS

Gauss et al., "Synthesis of Acetic Acid and Acetic Acid Anhydride from Methanol" B. Cornils and W.A. Herrmann, Applied Homogeneous Catalysis with Organometallic Compounds, Vol. 1, p. 104–138, (New York: VCH, 1996).

* cited by examiner

Primary Examiner—Alan L. Rotman
Assistant Examiner—Hector M. Reyes
(74) Attorney, Agent, or Firm—M. Susan Spiering

(57) ABSTRACT

A method and system is provided for producing acetic acid by the catalytic carbonylation of methanol with carbon monoxide to obtain a reaction product stream comprising acetic acid and a minor amount of acetaldehyde. The acetaldehyde content in the reaction product stream is reduced by oxidation to convert at least a portion of the acetaldehyde in the stream to acetic acid or further to $CO_2$ and $H_2O$. The oxidized stream may then be directed to the purification section, the reaction section, or both whereby the deleterious effects of acetaldehyde are reduced. Advantage of the present invention over conventional processes is the reduced need to dispose of acetaldehyde as waste and improved overall system efficiency in the production of acetic acid.

20 Claims, 1 Drawing Sheet

Figure 1:
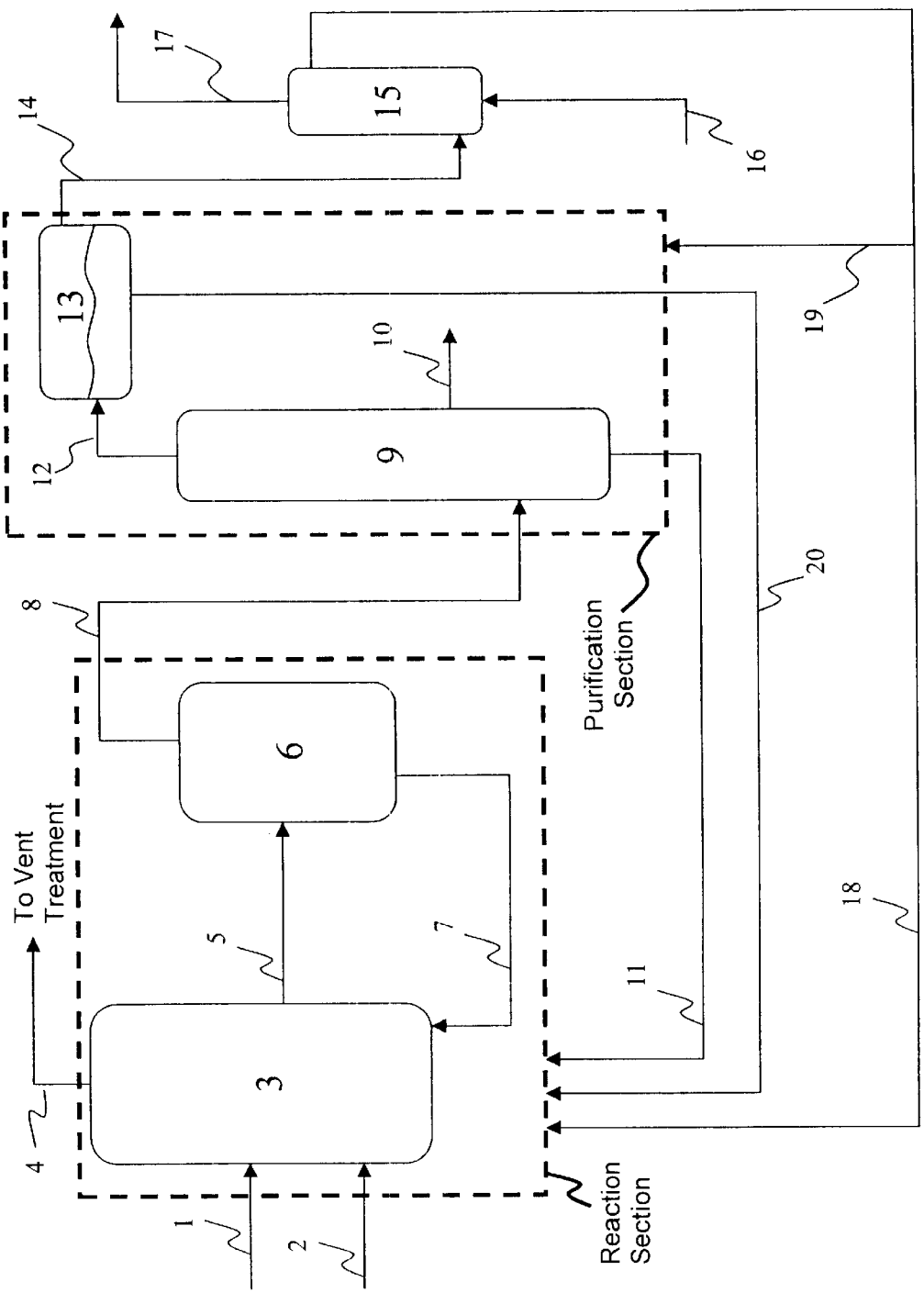

OXIDATION TREATMENT OF A RECYCLE STREAM IN PRODUCTION OF ACETIC ACID BY METHANOL CARBONYLATION

BACKGROUND OF THE INVENTION

1. Field of the Invention

The invention relates to an improved process for the production of acetic acid by methanol carbonylation.

2. The Related Art

An important process for the production of acetic acid is the carbonylation of methanol with carbon monoxide in a liquid reaction medium. The reaction is generally carried out in the presence of a catalyst, e.g., a Group VIII metal catalyst such as rhodium, a halogen containing catalyst promoter, e.g., methyl iodide, and water. An ionic catalyst stabilizer/co-promoter such as lithium iodide may also be present. A disadvantage of this process is that, in addition to the desired acetic acid, various amounts of undesirable impurities are also produced, e.g. permanganate reducing compounds (PRC's) including carbonyl compounds such as acetaldehyde, unsaturated aldehydes such as crotonaldehyde and 2-ethylcrotonaldehyde, saturated aldehydes other than acetaldehyde such as butyraldehyde and 2-ethylbutyraldehyde, and ketones such as acetone and methyl ethyl ketone, all of which are involved in the determination of "permanganate time," an important commercial test which the acetic acid product must pass for many end uses. Other undesirable impurities produced in the methanol carbonylation process are propionic acid which reacts similarly to acetic acid in the production of products such as vinyl acetate but often has an adverse effect on the properties of such products, and when methyl iodide is used as a catalyst promoter, higher alkyl iodides, e.g., $C_2$–$C_{12}$ alkyl iodides such as ethyl iodide and hexyl iodide which are more difficult to remove from acetic acid by distillation than methyl iodide and which among other adverse effects, poison the catalysts generally used in the production of vinyl acetate from acetic acid.

It is believed that, in addition to reducing the selectivity to acetic acid of the methanol carbonylation process, the acetaldehyde formed in the reaction is instrumental in the formation of several of the foregoing impurities by undergoing further reaction. Thus, acetaldehyde under typical reaction conditions may form various hydroxyaldehydes by aldol condensation and cross-aldol condensation, which are then dehydrated to form unsaturated aldehydes such as crotonaldehyde and 2-ethylcrotonaldehyde. Moreover, because of the presence of hydrogen in the reaction section due to the water gas shift reaction, some of the acetaldehyde may be reduced to ethanol, which is then carbonylated to propionic acid. Finally, when methyl iodide is present as a catalyst promoter and/or an ionic iodide such as lithium iodide is used as a catalyst stabilizer/co-promoter, such compound may react with acetaldehyde or a carbonyl compound synthesized from acetaldehyde to form one or more $C_2$–$C_{12}$ alkyl iodides which are more difficult to separate from acetic acid than is methyl iodide.

In view of the reduction of selectivity to acetic acid caused by the formation of acetaldehyde and the adverse effects resulting from the presence in the acetic acid product of even small amounts of acetaldehyde and compounds formed from acetaldehyde both during the methanol carbonylation reaction, and the purification of the acetic acid product, a method for reducing the amount of acetaldehyde in any part of the reaction and/or purification sections of the system is desirable.

U.S. Pat. No. 3,769,329 discloses a process for the production of acetic acid by the carbonylation of methanol with carbon monoxide in the presence of a catalyst system comprising rhodium and a halogen component wherein the halogen is iodine or bromine.

U.S. Pat. Nos. 5,001,259; 5,026,908; and 5,144,068 disclose processes for the production of acetic acid by the carbonylation of methanol with carbon monoxide in a liquid medium containing a rhodium catalyst stabilized with an iodide salt along with an alkyl iodide, an alkyl acetate and an unusually low concentration of water.

Various methods for reducing impurity levels in acetic acid production processes have been disclosed. U.S. Pat. Nos. 5,155,265, 5,155,266, and 5,202,481 disclose the purification of acetic acid made by low water carbonylation of methanol with carbon monoxide and containing iodide, unsaturates and carbonyl impurities, by treating the final product with ozone.

U.S. Pat. No. 5,625,095 discloses a process for the production of acetic acid by the carbonylation of methanol with carbon monoxide in the presence of a rhodium catalyst, iodide salts and methyl iodide wherein the acetaldehyde concentration in the reaction liquid is maintained at 400 ppm or lower by contacting the liquid containing the carbonyl impurities with water to separate and remove such impurities.

M. Gauss, A. Seidel, G. P. Torrence and P. Heymann's, "Synthesis of Acetic Acid and Acetic Acid Anhydride from Methanol" in B. Cornils and W. A. Herrmann, Applied Homogeneous Catalysis with Oryanometallic Compounds, Vol. 1, p. 104–138, (New York: VCH, 1996), is a survey description of the process of synthesizing acetic acid and acetic anhydride by the carbonylation of methanol and methyl acetate respectively with carbon monoxide using metal complexes such as those of rhodium and cobalt as catalyst and a methyl halide such as methyl iodide as promoter. FIG. 1 on page 114 of volume 1, is a flow diagram showing a process for the production of acetic acid using a rhodium catalyst. The reactor liquid is passed to a flasher where acetic acid product and a majority of the light ends components are separated as vapor from the catalyst solution and are then fed to a light ends distillation column where such light ends components are further separated as overhead from the bulk of the acetic acid product, such overhead being condensed into two phases, one being predominantly aqueous and the other predominately organic.

U.S. Pat. No. 6,143,930 discloses processes for the synthesis of acetic acid by carbonylation of methanol, including the step of removing the acetaldehyde in the system by twice distilling the aqueous phase, i.e., the lighter liquid phase of the overhead from the light ends distillation column. Optionally, the overhead from the last column may be subjected to an aqueous extraction to recover residual methyl iodide for recycle before sending the extract containing acetaldehyde to waste treatment.

All patents and publications referred to herein are hereby incorporated herein by reference in their entireties.

SUMMARY OF THE INVENTION

The present invention relates to a process and a system for producing acetic acid by the catalytic carbonylation of methanol with carbon monoxide to obtain a reaction product stream comprising acetic acid and a minor amount of acetaldehyde. The acetaldehyde in the reaction product stream is partially converted by oxidation to acetic acid or further to $CO_2$ and $H_2O$. The stream may then be directed to the purification section, the reaction section, or both, thereby reducing the deleterious effects of acetaldehyde. In conventional systems, acetaldehyde is isolated for removal as a waste stream component. One of the advantages of the present invention over conventional processes is the elimination of at least one waste stream or reducing the quantity of waste produced. Additionally, the conversion of acetaldehyde to acetic acid through the oxidation process increases the efficiency of the overall process.

DRAWING

FIG. 1 is a schematic diagram of an embodiment of the process of the present invention.

DETAILED DESCRIPTION OF THE INVENTION

Processes for the synthesis of acetic acid by the catalytic carbonylation of methanol with carbon monoxide are well known in the art as exemplified by the disclosures of the previously cited references. Methanol and CO are reacted in the presence of a catalyst system which may comprise, for example, a Group VIII metallic element, particularly Rh, Ir, Co, Ni, Ru, Pd or Pt, and most often Rh or Ir, a halogen promoter, most often a hydrogen halide or organic halide, particularly an alkyl iodide such as methyl iodide, a stabilizer/copromoter, which is a salt of a metal of Group IA or IIA of the Periodic Table, or a quaternary ammonium or phosphosium salt, particularly an iodide or acetate salt and most often lithium iodide, or lithium acetate. The active catalyst may be a complex of the Group VIII metal, and in some cases may be added to the reaction section as a pre-formed complex rather than the described individual catalyst components. The catalyst system is dissolved or dispersed in a liquid medium comprising methyl acetate, acetic acid, a finite amount of water, e.g., at least about 0.1 wt. % and up to about 15 wt. % or higher, and any other solvent component compatible with the other compounds present.

A suitable catalyst system for the process includes rhodium as the Group VIII metal, methyl iodide as the halogen catalyst promoter, lithium iodide as catalyst stabilizer/copromoter, all dissolved or dispersed in a liquid medium comprising methyl acetate, acetic acid, and a relatively low amount of water in the range of about 0.1 wt. % to about 8 wt. % based on the total weight of reaction liquid.

During a period of active reaction, methanol and CO are continuously fed to a reactor containing reaction liquid in which a desired partial pressure of CO is maintained. As mentioned previously and discussed hereinafter, the reaction liquid may contain small amounts of undesirable impurities in addition to the desired components identified previously, e.g., acetaldehyde and other carbonyl containing PRC's, and propionic acid.

To prevent the accumulation of inert gases, a gaseous purge is withdrawn from the top of the reactor and treated to recover valuable condensables such as methyl iodide and methyl acetate. The remaining gases are sent to a flare. Reaction liquid is withdrawn from the reactor and fed to a flasher where a reduction in pressure results in the vaporization of the lighter components from the reaction mixture, the remainder of the reaction mixture comprising acetic acid and the Group VIII metal catalyst may be recycled to the reactor. The vapors from the flasher are fed to a light ends or splitter column from which a crude acetic acid product is withdrawn as a liquid side draw or base product (as described in U.S. Pat. No. 5,144,068) and sent to further purification and the overhead vapors are condensed and separated into a light aqueous phase and a heavy organic phase. The light aqueous phase contains a preponderance of water, a lower but significant amount of acetic acid, and much smaller amounts of methanol, methyl iodide, and methyl acetate. Acetaldehyde and other PCR's, which are by-products of the initial reaction or are formed subsequently from further reaction of acetaldehyde, are also present. The heavy organic phase contains predominately methyl iodide with some methyl acetate, a minor amount of water, and a typically smaller percentage of acetaldehyde, than the light aqueous phase. The heavy organic phase is either recycled directly to the reaction section or recycled after further processing, including optionally processing via oxidation.

The light aqueous phase of the overhead condensate of the light ends column is typically used as reflux and a portion is recycled directly to the reaction section. As used herein, the phrase "reaction section" refers to the reactor and flasher components of the system collectively. In some processes, the light aqueous phase is first fed to an acetaldehyde removal system as disclosed, for example, in previously cited U.S. Pat. No. 6,143,930 and U.S. Pat. No. 3,769,329. In one variation of an acetaldehyde removal system the light aqueous phase of the light ends column overhead condensate is fed to a first distillation column, termed an "acetaldehyde concentrator", which serves to separate most of the acetaldehyde, methyl iodide, and methyl acetate as overhead from a heavier fraction comprising acetic acid and water, which is recycled to the purification section. The latter overhead is then fed to a second distillation column, termed an "acetaldehyde stripper", which serves to separate most of the acetaldehyde in this stream, from a heavier fraction comprising methyl iodide and methyl acetate, which is recycled to the purification section. The latter overhead comprising an increased concentration of acetaldehyde and some heavier components such as methyl iodide is then subjected to an extraction with water to obtain an aqueous extract comprising most of the acetaldehyde and an organic raffinate comprising the less water-soluble components of the stream such as methyl iodide, which is recycled to the purification section. The aqueous acetaldehyde stream is disposed of as waste. As used herein, the phrase "purification section" refers to the distillation and separator/decanter components of the system collectively.

The present invention provides a process in which the need to isolate and dispose of acetaldehyde as a waste stream is eliminated. However, it is understood that the present invention may be used in conjunction with a process including acetaldehyde isolation and removal as waste. In one embodiment of the invention, at least a portion of the acetaldehyde in the light aqueous phase of the overhead of the light ends column is oxidized to convert the acetaldehyde to acetic acid, or further to $CO_2$ and $H_2O$, before recycling to the purification section or forwarding to the reaction section. Alternatively, the oxidized portion of the light phase stream may be split and returned to both the reaction section and the purification section. Wherever it is stated herein that a stream is forwarded to the reaction section or the purification section, the path to the reaction section or purification section may not be direct but may be by way of an intermediate point such as for further purification or treatment before the significant components of the stream actually enter the reaction section. Such light aqueous phase may contain about 0.05 to about 5 wt. % of acetaldehyde, about 0.1 to about 5 wt. % of methyl iodide, about 0.1 to about 10 wt. % of methyl acetate, about 10 to about 45 wt. % of acetic acid, and the balance is water. Typically the light aqueous phase from the light ends column overhead contains about 0.5 to 2 wt. % of acetaldehyde, about 2 wt. % of methyl iodide, about 6 wt. % of methyl acetate, about 2 wt. % of methanol, about 20 wt. % of acetic acid, and the balance is water.

In other embodiments of the present invention, depending on the configuration of the process equipment, streams or portions of streams other than the light aqueous phase may be oxidized to reduce acetaldehyde content. In other words, any post reaction stream, or a portion thereof, containing acetaldehyde may be oxidized to convert the acetaldehyde to acetic acid or further to $CO_2$ and $H_2O$. One reason for converting acetaldehyde in the light phase is to eliminate the need to isolate and dispose of the acetaldehyde as a waste product. Another reason is to convert unwanted acetaldehyde to the desired product, acetic acid. A third reason is to prevent the formation of other undesirable impurities from further reaction of acetaldehyde.

One embodiment of the present invention is to oxidize the aqueous extraction of acetaldehyde from the acetaldehyde stripper overhead stream before such extract is recycled to the reaction section. Such an extract, before oxidation, will contain from about 20 to about 25 wt. % of acetaldehyde, from about 2 to about 5 wt. % of dimethyl ether, from about 65 to about 75 wt. % of water, and from about 0.5 to about 1 wt. % of methyl iodide. In a typical process, the aqueous extract may contain about 25 wt. % of acetaldehyde, about 3 wt. % of dimethyl ether, about 70 wt. % of water, and about 1 wt. % of methyl iodide. The oxidized stream may then be recycled to the purification section or forwarded to the reaction section.

In another embodiment of the present invention, a stream, which may be subjected to the oxidation treatment, is the dry organic stream from the overhead of the acetaldehyde stripper. This stream may contain from about 45 to about 75 wt. % of acetaldehyde, from about 5 to about 15 wt. % of dimethyl ether, and from about 20 to about 40 wt. % of methyl iodide. In a typical process, this stream is, for example, about 60 wt. % of acetaldehyde, about 10 wt. % of dimethyl ether, and about 30 wt. % of methyl iodide. The oxidized stream may then be recycled to the purification section or forwarded to the reaction section rather than subjected to an extraction treatment.

In another embodiment, the overhead stream of the acetaldehyde concentrator is subjected to an oxidation treatment in accordance with the present invention. This stream may contain, for example, from about 5 to about 10 wt. % of acetaldehyde, from about 0.1 to about 40 wt. % of methyl iodide, from about 45 to about 65 wt. % of methyl acetate, and about 2 to about 5 wt. % of water. In a typical process, this stream may have a composition of about 8 wt. % of acetaldehyde, about 34 wt. % of methyl iodide, about 54 wt. % of methyl acetate, and about 4 wt. % of water. The oxidized stream may then be recycled to the purification section or forwarded to the reaction section rather than being fed to the acetaldehyde stripper.

In yet another embodiment of the present invention, and not shown in FIG. 1, acetaldehyde can be extracted from the heavy phase recycle, 20, into a separate circulating aqueous phase. This separate aqueous phase is forwarded to the oxidation reactor, 15. The extractor, wherein these streams are contacted, serves a dual purpose. First, it allows the circulating aqueous phase to extract acetaldehyde from the heavy phase recycle, 20. Second, it allows oxidation reaction products to be extracted by the heavy phase recycle from the circulating aqueous stream and thus recycled to the carbonylation reactor, 3. It may also be desirable to purge the circulating aqueous phase to further minimize the accumulation of oxidation reaction products. Any aqueous recycle stream within the carbonylation process or water from and outside source, may serve as a source for such a purge.

This alternative embodiment of the invention thus involves a process for the production of acetic acid by the carbonylation of methanol, in a system comprising a reaction section and a purification section, comprising the steps of: (a) producing a reaction section product stream comprising acetic acid, acetaldehyde, and water in a reaction section comprising a reactor and a flasher; (b) directing at least a portion of the reaction section product stream to a purification section comprising a light ends distillation column to separate the reaction section product stream into component streams comprising a heavy phase stream and a light phase stream wherein the heavy phase stream is comprised of acetic acid, acetaldehyde and water; (c) directing at least a portion of the heavy phase stream to an extractor means to extract acetaldehyde from the heavy phase stream and forming an aqueous phase stream comprising some acetaldehyde; (d) directing and circulating at least a portion of the aqueous phase stream to an oxidizing means to oxidize at least a portion of the aqueous phase stream and forming an oxidized effluent stream; (e) circulating at least a portion of the effluent stream between an extractor means and the oxidizing means; (f) withdrawing at least a portion of the oxidized aqueous phase stream from the extractor means and directing the withdrawn portion of the oxidized aqueous phase stream to a portion of the system selected from the group consisting of the reaction section, the purification section, and both the reaction section and the purification section.

Another option is to directly oxidize the heavy phase recycle, 20. The heavy phase recycle, 20, may be forwarded to the oxidation reactor, 15, and the effluent directed to the carbonylation reactor, 3. However, oxidation reaction byproducts, such as iodine, may form and be operationally problematic.

This alternate embodiment to directly oxidize the heavy phase involves a process for the production acetic acid by the carbonylation of methanol, in a system comprising a reaction section and a purification section, comprising the steps of: (a) producing a reaction section product stream comprising acetic acid, acetaldehyde, and water in a reaction section comprising a reactor and a flasher; (b) directing at least a portion of the reaction section product stream to a do purification section comprising a light ends distillation column to separate the reaction section product stream into component streams comprising a heavy phase stream and a light phase stream wherein the heavy phase stream is comprised of acetic acid, acetaldehyde and water; (c) directing at least a portion of the heavy phase stream to an oxidation means to oxidize at least a portion of the heavy phase stream; and (d) withdrawing at least a portion of the oxidized heavy phase stream from the oxidizing means and directing the withdrawn portion of the oxidized heavy phase stream to a portion of the system selected from the group consisting of the reaction section, the purification section, and both the reaction section and the purification section.

The oxidation of the acetaldehyde in any stream to be treated in accordance with this invention may be accomplished with any oxidizing agent capable of converting acetaldehyde to acetic acid or further to $CO_2$ and $H_2O$.

Suitable oxidizing agents may be gaseous at normal temperature and pressure ("NTP"). Examples of such oxidizing agents are air or pure oxygen. Alternatively oxygen diluted with air or an inert gas such as nitrogen or even air diluted with an inert gas such as nitrogen is suitable. Other examples of suitable oxidizing agents, which are gaseous at NTP, are ozone or ozone diluted with an inert gas such as nitrogen or argon.

When a gaseous oxidant such as ozone, oxygen, or air is employed, the oxidation may be carried out by bubbling the oxidant through a volume of the stream being treated. The oxidation step may take place in the presence of oxidation catalysts which do not adversely react with any of its components.

Suitable oxidizing agents may also be liquid at NTP. Oxidation with liquid oxidants such as peracetic acid or hydrogen peroxide may be carried out by mixing the stream being treated with the oxidant in a stirred reaction section. The effective molar ratio of the oxidants to the acetaldehyde in the oxidation step is over a wide range. Generally, molar ratios of 0.5 to 10 are suitable, with ratios of 0.5 to 4 being more likely for most equipment and oxidants.

Whether the oxidant is a liquid or gas, the temperature and pressure of the oxidation is not critical as long as flammability or explosion limits are not exceeded. In this regard, particular care should be exercised when using oxidizing agents such as hydrogen peroxide which can be explosive at elevated temperatures. Generally, oxidation processes in accordance with the present invention will take place at temperatures within the range of about 15° C. to about 250° C. and at pressures in the range of about 1 Bar to about 25 Bars, with most processes taking place at a temperature of oxidation within the range of about 50° C. to about 200° C. and pressure within the range of about 1 Bar to about 10 Bars. However, oxidation may take place at much higher pressures, particularly when using oxidants which are gaseous at NTP. Oxidation pressures of 70 Bars or more are useful with gaseous oxidants, with pressures up to 40 Bars being more likely for most process equipment and oxidants. The temperature and pressure at which oxidation occurs is dependent on the particular oxidant. Generally, residence times for the oxidation process will be within the range from about 10 minutes to about 10 hours, with most processes being within the range from about 1 hour to about 3 hours.

For most processes and equipment using peracetic acid and hydrogen peroxide as oxidants, the oxidation temperature will fall within the range of from about 15° C. to about 75° C. For most processes and equipment using oxygen and/or air as oxidants, the oxidation temperature range will be from about 100° C. to about 250° C. When ozone is used as an oxidant, in most processes and equipment, the oxidation temperatures will range form about 15° C. to about 75° C.

The oxidation treatment of this invention may be carried out on substantially the entire amount or only a portion of the acetaldehyde in any of the streams described previously, either by oxidizing substantially all the acetaldehyde in only a portion of the stream, or oxidizing only a portion of the acetaldehyde in the entire stream, or a combination of the two approaches. Moreover, it may be desirable in some instances to practice the oxidation treatment of the invention on more than one of the described acetaldehyde containing streams. Obviously, depending on how the process is specifically designed, carrying out an oxidation treatment on any of the described acetaldehyde containing streams will generally eliminate the need for units of an acetaldehyde removal system downstream of the stream subjected to such oxidation treatment or allow for reduced capacity of such downstream units thereby reducing or entirely eliminating a waste stream. The oxidation treatment method also results in an improved overall efficiency in the production of acetic acid by converting acetaldehyde to acetic acid.

Referring now to FIG. 1, continuous streams of methanol and carbon monoxide are fed through lines 1 and 2 respectively into stirred reactor 3 containing a reaction liquid comprising an acetic acid solution of rhodium as catalyst, methyl iodide as halogen promoter, lithium iodide as salt copromoter/stabilizer, water, unreacted methanol and carbon monoxide and impurities such as acetaldehyde and other PRC's, and higher alkyl iodides. Quantities of reactant streams entering, and catalyst components in the reaction section, as well as process parameters such as temperature, pressure and residence time, are within the ranges well known in the art for the carbonylation of methanol with carbon monoxide to produce acetic acid. Gases formed in the reaction section are withdrawn through line 4 and are sent to vent recovery for the separation of components suitable for recycle to the reaction. Reaction liquid is continuously withdrawn from reactor 3 through line 5 and is fed to flasher 6 where a reduction of pressure causes a portion of the acetic acid and most of the lower boiling compounds to be flashed off as vapor leaving a solution of the heavier components of the catalyst system. The liquid remaining in flasher 6 is recycled through line 7 to reactor 3 while the vapors from flasher 6 are fed through line 8 to light ends or "splitter" column 9 where most of the lower boiling components including methyl iodide, methyl acetate, and acetaldehyde, and a portion of the water are removed overhead. A crude aqueous acetic acid liquid is withdrawn from light ends column 9 through line 10 and sent to the acetic acid recovery system (not shown). A bottoms fraction comprising some acetic acid and higher boiling components is withdrawn from light ends column 9 through line 11 and recycled to the reaction section. The overhead vapor stream from the light ends column is condensed and fed through line 12 to separator/decanter 13, where the condensate separates into a light aqueous phase containing a preponderance of water, a substantial although minor proportion of acetic acid and much lower amounts of methyl iodide, methyl acetate and methanol, and a heavy organic phase containing a minor amount of water, a much larger percentage of methyl iodide and a smaller percentage of acetaldehyde than are present in the light aqueous phase. The light aqueous phase is fed through line 14 to oxidation vessel 15, to which is also fed an oxidizing agent through line 16 which oxidizes most of the acetaldehyde in the light aqueous phase to acetic acid or further to $CO_2$ and $H_2O$. Oxidation vessel 15 may be selected from a number of types of reactors such as a continuously stirred reactor or a co-current or counter current flow reactor in which any can be used with a catalyst. The reactor may also be a stirred vessel reactor or co-current or counter current reactor which may contain a fixed bed of oxidation catalyst. If the oxidizing agent is fed as a gas, or a gas by-product such as $CO_2$ is produced, then the spent gas may be withdrawn through line 17, scrubbed to remove compounds such as methyl iodide and methyl acetate which may be recycled to the purification section or forwarded to the reaction section and a portion of the scrubbed gas is vented to remove inert gases such as nitrogen and carbon dioxide and a portion may be recycled to oxidation vessel 15 with makeup oxidizing gas. The treated light aqueous phase is withdrawn from oxidation vessel 15 and recycled to the purification section through line 19 or forwarded to the reaction section through line 18, or to both the purification section and the reaction section, while the heavy organic phase from separator/decanter 13 is directly recycled through line 20 to the reaction section.

The following detailed examples illustrate the practice of the present invention in various forms. The principles of the invention and modifications thereof will be understood in view of the following examples.

EXAMPLES 1–11

Examples 1–11 (Run No. 1–11) set forth in Table I demonstrate control experiments using nitrogen and the use of air as an oxidizing agent in accordance with the present invention over various temperatures and pressures. Specifically, Examples 1–2 are comparative examples demonstrating the low levels of acetaldehyde conversion in the absence of an oxidizing agent used in accordance with the present invention. The words "Example" and "Runs" or "Run No." and "Example No." are used interchangeably herein Examples 1–11 are experiments using a batch autoclave conducted on light phase streams removed from a separator/decanter 13 from the overhead condensate of light ends column 9 shown in FIG. 1 and employed in the purification of the product of a typical process for producing acetic acid by the carbonylation of methanol with carbon monoxide utilizing a rhodium catalyst, methyl iodide as halogen promoter, and lithium iodide as salt stabilizer/copromoter.

Table IV identifies the composition of the light phase stream used in each Run and the conditions (including temperature, pressure, and oxidation run time) under which each experiment was conducted. Table I also reports the acetaldehyde conversion as a percentage decrease of the acetaldehyde concentration in the light phase stream following the oxidation process. All compositions were determined by GC analysis.

TABLE I

Results of Control Runs Using Nitrogen and Oxidation Runs Using Air

| Run No. | Temp (° C.) | Pressure (Bars) | Oxidant | Run Time (min.) | wt % Initial Acetaldehyde | wt % Final Acetaldehyde | % Acetaldehyde Conversion |
|---|---|---|---|---|---|---|---|
| 1 | 150 | 13.3 | $N_2$ | 120 | 0.17 | 0.15 | 12 |
| 2 | 150 | 13.3 | $N_2$ | 120 | 0.17 | 0.13 | 23 |
| 3 | 150 | 14.4 | Air | 120 | 0.17 | 0.003 | 99 |
| 4 | 150 | 14.4 | Air | 60 | 0.39 | 0.21 | 46 |
| 5 | 150 | 14.4 | Air | 120 | 0.39 | 0.02 | 95 |
| 6 | 175 | 14.4 | Air | 60 | 0.39 | 0.07 | 82 |
| 7 | 175 | 14.4 | Air | 120 | 0.39 | 0.03 | 92 |
| 8 | 175 | 34.6 | Air | 120 | 0.39 | 0.004 | 99 |
| 9 | 125 | 34.6 | Air | 180 | 0.58 | 0.10 | 83 |
| 10 | 175 | 34.6 | Air | 90 | 0.58 | 0.02 | 97 |
| 11 | 200 | 68.1 | Air | 60 | 0.58 | 0.01 | 98 |

Examples 1–2 are control runs showing the level conversion of acetaldehyde ("AcH") in the absence of an oxidizing agent. In these runs, nitrogen, rather than air, was charged in the batch autoclave reaction section. These experiments resulted in acetaldehyde conversion levels 12% and 23% for runs 1 and 2 respectively.

Examples 3–11 demonstrate acetaldehyde conversion levels ranging from 46% to 99% when air, as the oxidizing agent, is charged to the system at the various temperatures and pressures set forth in Table I. At an air pressure of 14.4 Bars, a temperature of 150° C., and a reaction time of one hour, 46% of the acetaldehyde was converted in Example 4. In Example 8, at an air pressure of 34.6 Bars, a temperature of 175° C., and a reaction time of two hours, 99% of the acetaldehyde was converted.

EXAMPLES 12–23

Examples 12–23 (Runs 12–23) set forth in Table II demonstrate the use of hydrogen peroxide ($H_2O_2$) as an oxidizing agent in accordance with the present invention over various temperatures and concentrations.

Runs 12–23 are experiments using the batch autoclave conducted, again, on light phase streams removed from a separator/decanter 13 from the overhead condensate of light ends column 9 shown in FIG. 1 and employed in the purification of the product of a typical process for producing acetic acid by the carbonylation of methanol with carbon monoxide utilizing a rhodium catalyst, methyl iodide as halogen promoter, and lithium iodide as salt stabilizer/copromoter.

Table IV identifies the composition of the light phase stream used in each run. Table II sets forth the conditions under which each run was conducted. Table II also reports the acetaldehyde conversion as a percentage decrease of the acetaldehyde concentration in the light phase stream following the oxidation process. All compositions were determined by GC analysis.

TABLE II

Results of Oxidation Runs Using Hydrogen Peroxide

| Run No. | Temp. (° C.) | Run Time (hr.) | $H_2O_2$ mmols | $H_2O_2$: Acetaldehyde mole ratio | % Acetaldehyde Conversion |
|---|---|---|---|---|---|
| 12 | 25 | <1 | 0 | 0 | 0 |
| 13 | 25 | 24 | 0 | 0 | 7 |

TABLE II-continued

Results of Oxidation Runs Using Hydrogen Peroxide

| Run No. | Temp. (° C.) | Run Time (hr.) | $H_2O_2$ mmols | $H_2O_2$: Acetaldehyde mole ratio | % Acetaldehyde Conversion |
|---|---|---|---|---|---|
| 14 | 60 | 24 | 0 | 0 | 7 |
| 15 | 25 | <1 | 3.2 | 0.6 | 0 |
| 16 | 25 | 24 | 3.2 | 0.6 | 22 |
| 17 | 60 | 24 | 3.2 | 0.6 | 41 |
| 18 | 25 | <1 | 6.3 | 1.1 | 0 |

TABLE II-continued

Results of Oxidation Runs Using Hydrogen Peroxide

| Run No. | Temp. (° C.) | Run Time (hr.) | H₂O₂ mmols | H₂O₂: Acetaldehyde mole ratio | % Acetaldehyde Conversion |
|---|---|---|---|---|---|
| 19 | 25 | 24 | 6.3 | 1.1 | 46 |
| 20 | 60 | 24 | 6.3 | 1.1 | 54 |
| 21 | 25 | <1 | 12.4 | 2.6 | 0 |
| 22 | 25 | 24 | 12.4 | 2.6 | 28 |
| 23 | 60 | 24 | 12.4 | 2.6 | 62 |

The data in Tables II demonstrates that hydrogen peroxide is effective to convert acetaldehyde in acetic acid production process streams. It is seen that the percent conversion of acetaldehyde generally rises with increasing hydrogen peroxide:AcH mole ratio, time of reaction, and temperature.

EXAMPLES 24–35

Examples 24–35 (Runs 24–35) set forth in Table III demonstrate the use of peracetic acid ("AcO₂H") as an oxidizing agent in accordance with the present invention over various temperatures and concentrations.

Runs 24–35 are experiments using the batch autoclave conducted, again, on light phase streams removed from a separator/decanter 13 from the overhead condensate of light ends column 9 shown in FIG. 1 and employed in the purification for the product of a typical process of producing acetic acid by the carbonylation of methanol with carbon monoxide utilizing a rhodium catalyst, methyl iodide as halogen promoter, and lithium iodide as salt stabilizer/copromoter. Table IV identifies the composition of each light phase stream used in each run.

Table III sets forth the conditions under which each run was conducted. Table III also reports the acetaldehyde conversion as a percentage decrease of the acetaldehyde concentration in the light phase stream following the oxidation process. All compositions were determined by GC analysis.

TABLE III

Results of Oxidation Runs Using Pwracetic Acid

| Run No. | Temp. (° C.) | Run Time (hr.) | AcO₂H mmols | AcO₂H: Acetaldehyde mole ratio | % Acetaldehyde Conversion |
|---|---|---|---|---|---|
| 24 | 25 | <1 | 0 | 0 | 0 |
| 25 | 25 | 24 | 0 | 0 | 4 |
| 26 | 60 | 24 | 0 | 0 | 9 |
| 27 | 25 | <1 | 5.0 | 2.1 | 74 |
| 28 | 25 | 24 | 5.0 | 2.1 | 77 |
| 29 | 60 | 24 | 5.0 | 2.1 | 99 |
| 30 | 25 | <1 | 10.0 | 4.1 | 100 |
| 31 | 25 | 24 | 10.0 | 4.1 | 100 |
| 32 | 60 | 24 | 10.0 | 4.1 | 100 |
| 33 | 25 | <1 | 20.5 | 8.5 | 100 |
| 34 | 75 | 24 | 20.5 | 8.5 | 100 |
| 35 | 60 | 24 | 20.5 | 8.5 | 100 |

TABLE IV

Light Phase Compositions

| | Light Phase Composition (wt %) | | | |
|---|---|---|---|---|
| | Runs 1–3 | Runs 4–8 | Runs 9–11 | Runs 12–35 |
| Acetaldehyde | 0.2 | 0.4 | 0.6 | 1.5 |
| Methyl Iodide | 1.4 | 2.2 | 1.2 | 2 |
| Methyl Acetate | 3.4 | 4.3 | 5.3 | 6 |
| Methanol | 2.6 | 3.3 | 3.4 | 2 |
| Water & Acetic Acid | 92.4 | 89.8 | 89.5 | 89.5 |

As shown by the data in Table III, under certain conditions, peracetic acid is a more effective liquid oxidant of acetaldehyde than is hydrogen peroxide. At an AcO₂H:AcH mole ratio of 2.1, most of the acetaldehyde is converted at reaction times less than 24 hours at 25° C., and substantially all the acetaldehyde is converted at 60° C. At AcO₂H:AcH mole ratios of at least 4.14, 100% of the acetaldehyde was converted at less than 24 hours regardless of the temperature.

The Examples described above demonstrate that higher levels of acetaldehyde conversion may generally be achieved by increasing the concentration of oxidizing agents, the temperature, total pressure, or residence time or a combination of these four variables. For example, comparing Examples 4 and 5 demonstrates the dependence of the acetaldehyde conversion on residence time. With all variables being held constant except for residence time, the percent of acetaldehyde conversion increases from 46% to 95% by increasing the residence time from one to two hours. Comparing Examples 4 and 6 demonstrates an increase of acetaldehyde conversion from 46% to 82% by increasing the temperature from 150° C. to 175° C. Likewise, comparing Examples 7 and 8, an increase in acetaldehyde conversion from 92% to 99% was achieved by increasing pressure from 14.4 Bars to 34.6 Bars.

As mentioned above, the process of the present invention is operative over a wide range of temperatures and pressures. By changing the process parameters set forth in Table I, one can optimize the conversion of acetaldehyde over this wide range of temperatures, pressures, and residence times. Of course, it is understood that most commercial processes will be designed to achieve a balance among the parameters that is economically attractive. Additionally, when using potentially explosive and flammable oxidizing agents such as oxygen and peroxide, considerable care should be observed when operating at high temperatures and pressures.

The foregoing disclosure and description of the invention are illustrative and explanatory thereof, and variations will be apparent to those skilled in the art, and are considered to be within the spirit and scope of the Claimed invention.

We claim:

1. A process for the production of acetic acid by the catalytic carbonylation of methanol with carbon monoxide, in a system comprising a reaction section and a purification section, comprising the steps of:
   (a) producing a stream comprising acetic acid and acetaldehyde;
   (b) reducing the acetaldehyde content of at least a portion of the stream by treating at least a portion of the stream with an oxidizing agent; and
   (c) directing at least a portion of the treated stream to a portion of the system selected from the group consisting of the reaction section, the purification section, and both the reaction section and the purification section.

2. The process of claim 1 wherein the treatment with the oxidizing agent takes place at a temperature in the range of about 15° C. to about 250° C. and at a pressure in the range of about 1 Bar to about 70 Bars.

3. The process of claim 2 wherein the oxidizing agent is selected from the group consisting of oxygen, air, and mixtures thereof.

4. The process of claim 2 wherein the oxidizing agent is a peroxide.

5. The process of claim 4 wherein the peroxide is selected form the group consisting of peracetic acid, hydrogen peroxide, and mixtures thereof.

6. The process of claim 2 wherein the oxidizing agent is ozone.

7. The process of claim 2 wherein the oxidation takes place in the presence of an oxidation catalyst.

8. The process of claim 2 wherein the oxidation agent is a liquid and the molar ratio of the liquid oxidant to acetaldehyde is from about 0.5:1 to about 4:1.

9. A process for the production of acetic acid by the carbonylation of methanol, in a system comprising a reaction section and a purification section, comprising the steps of:
(a) producing a reaction section product stream comprising acetic acid, acetaldehyde, and water in a reaction section comprising a reactor and a flasher;
(b) directing at least a portion of the reaction section product stream to a purification section comprising a light ends distillation column to separate the reaction section product stream into component streams comprising a heavy phase stream and a light phase stream wherein the light phase stream is comprised of acetic acid, acetaldehyde and water;
(c) directing at least a portion of the light phase stream to an oxidation means to oxidize at least a portion of the light phase stream; and
(d) withdrawing at least a portion of the oxidized light phase stream from the oxidizing means and directing the withdrawn portion of the oxidized light phase stream to a portion of the system selected from the group consisting of the reaction section, the purification section, and both the reaction section and the purification section.

10. The process of claim 9 wherein the oxidization of the light phase stream takes place at a temperature in the range of about 15° C. to about 250° C. and a pressure in the range of about 1 Bar to about 70 Bars.

11. The process of claim 10 wherein the oxidization of the light phase stream takes place in the presence of an oxidizing agent selected from the group consisting of oxygen, air, and mixtures thereof.

12. The process of claim 10 wherein the oxidizing agent is a peroxide.

13. The process of claim 12 wherein the peroxide is selected form the group consisting of hydrogen peroxide, peracetic acid, and mixtures thereof.

14. The process of claim 10 wherein said oxidizing agent is ozone.

15. The process in accordance with claim 10 wherein the oxidation takes place in the presence of an oxidation catalyst.

16. The process of claim 10 wherein the oxidation agent is a liquid and the molar ratio of the liquid oxidant to acetaldehyde is from about 0.5:1 to about 4:1.

17. A process for the production acetic acid by the carbonylation of methanol, in a system comprising a reaction section and a purification section, comprising the steps of:
(a) producing a reaction section product stream comprising acetic acid, acetaldehyde, and water in a reaction section comprising a reactor and a flasher;
(b) directing at least a portion of the reaction section product stream to a purification section comprising a light ends distillation column to separate the reaction section product stream into component streams comprising a heavy phase stream and a light phase stream wherein the heavy phase stream is comprised of acetic acid, acetaldehyde and water;
(c) directing at least a portion of the heavy phase stream to an oxidation means to oxidize at least a portion of the heavy phase stream; and
(d) withdrawing at least a portion of the oxidized heavy phase stream from the oxidizing means and directing the withdrawn portion of the oxidized heavy phase stream to a portion of the system selected from the group consisting of the reaction section, the purification section, and both the reaction section and the purification section.

18. A process for the production acetic acid by the carbonylation of methanol, in a system comprising a reaction section and a purification section, comprising the steps of:
(a) producing a reaction section product stream comprising acetic acid, acetaldehyde, and water in a reaction section comprising a reactor and a flasher;
(b) directing at least a portion of the reaction section product stream to a purification section comprising a light ends distillation column to separate the reaction section product stream into component streams comprising a heavy phase stream and a light phase stream wherein the heavy phase stream is comprised of acetic acid, acetaldehyde and water;
(c) directing at least a portion of the heavy phase stream to an extractor means to extract acetaldehyde from the heavy phase stream and forming an aqueous phase stream comprising some acetaldehyde;
(d) directing and circulating at least a portion of the aqueous phase stream to an oxidizing means to oxidize at least a portion of the aqueous phase stream and forming an oxidized effluent stream;
(e) circulating at least a portion of the effluent stream between an extractor means and the oxidizing means;
(f) withdrawing at least a portion of the oxidized aqueous phase stream from the extractor means and directing the withdrawn portion of the oxidized aqueous phase stream to a portion of the system selected from the group consisting of the reaction section, the purification section, and both the reaction section and the purification section.

19. The process of claim 18 wherein an aqueous stream is contacted with the circulating aqueous phase and purged from the oxidized effluent stream.

20. The process of claim 18 wherein the oxidization of the heavy phase stream takes place in the presence of an oxidizing agent selected from the group consisting of oxygen, air, and mixtures thereof.

* * * * *